United States Patent
Wilhelm et al.

(10) Patent No.: US 9,017,700 B2
(45) Date of Patent: Apr. 28, 2015

(54) PRODUCTION OF A VIABLE, STORABLE WORM EGG SUSPENSION

(75) Inventors: Rudolf Wilhelm, Bischweier (DE); Allan Kund Roepstorff, Rodovre (DK); Christian Moliin Outzen Kapel, Rungstedt Kyst (DK)

(73) Assignee: Dr. Falk Pharma GmbH, Freiburg (DE)

( * ) Notice: Subject to any disclaimer, the term of this patent is extended or adjusted under 35 U.S.C. 154(b) by 1133 days.

(21) Appl. No.: 12/594,074

(22) PCT Filed: Mar. 31, 2008

(86) PCT No.: PCT/EP2008/002542
§ 371 (c)(1),
(2), (4) Date: Aug. 31, 2010

(87) PCT Pub. No.: WO2008/119534
PCT Pub. Date: Oct. 9, 2008

(65) Prior Publication Data
US 2011/0008390 A1    Jan. 13, 2011

(51) Int. Cl.
*A61K 39/002*    (2006.01)
*A01N 1/02*    (2006.01)
*A61K 35/62*    (2006.01)

(52) U.S. Cl.
CPC ............... *A01N 1/02* (2013.01); *A01N 1/0205* (2013.01); *A61K 35/62* (2013.01)

(58) Field of Classification Search
USPC ............... 424/269.1; 422/12, 40, 41; 435/260
See application file for complete search history.

(56) References Cited

U.S. PATENT DOCUMENTS

| 6,764,838 B2 * | 7/2004 | Weinstock et al. .......... 435/71.1 |
| 2005/0118655 A1 | 6/2005 | Weinstock et al. | |

FOREIGN PATENT DOCUMENTS

| EP | 1 530 972 A2 | 5/2005 |
| WO | WO 2007/076868 A2 | 7/2007 |

OTHER PUBLICATIONS

Ichhpujani et al (Medical Parasitology 3rd edition, Jaypee Brother Medical Publishers Ltd, India. Revised 2005).*
PCT International Preliminary Report on Patentability for International Patent Application PCT/EP2008/002542 mailed Nov. 19, 2009—English translation.
Boes, J., et al., "Embryonation and infectivity of *Ascaris suum* eggs isolated from worms expelled by pigs treated with albendazole, pyrantel pamoate, ivermectin or piperazine dihydrochloride", Veterinary Parasitology, Feb. 28, 1998, pp. 181-190, vol. 75, No. 2-3.
Elliott, D. et al., "Helminthic parasite exposure protects mice from colitis", Digestive and Liver Disease, May 2000, p. A26, vol. 32, Supplement 1.
Hunter, M. M., et al., "Review article: Helminths as therapeutic agents for inflamatory bowel disease", Alimentary Pharmacology & Therapeutics, Jan. 15, 2004, pp. 167-177, vol. 1, No. 2, Blackwell Scientific Publications, Ltd., Cambridge, Great Britain.
Reddy, A., et al., "The use of *Trichuris suis* and other helminth therapies to treat Crohn's disease", Parasitology Research, Apr. 2007, vol. 100, No. 5, pp. 921-927, Springer Verlag, Berlin, Germany.
Summers. Robert W., et al., "*Trichuris suis* seems to be safe and possibly effective in treatment of inflammatory bowel disease". American Journal of Gastroenterology, Sep. 2003, vol. 98, No. 9, pp. 2034-2041.
Summers, Robert W., et al., "*Trichuris suis* therapy in Chrohn's disease", GUT, Jan. 2005, vol. 54, No. 1, pp. 87-90.
PCT Search Report and Written Opinion for International Patent Application PCT/EP2008/002542 mailed Mar. 7, 2008.

* cited by examiner

*Primary Examiner* — Jennifer Graser
(74) *Attorney, Agent, or Firm* — Curatolo Sidoti Co., LPA; Joseph G. Curatolo; Salvatore A. Sidoti

(57) ABSTRACT

The present application describes a novel, advantageous purification method which guarantees the embryonation capability and the viability of a worm egg suspension. The *T. suis* worm eggs are first treated in a non-embryonated condition in a sulfuric acid solution at about =ph 2. Bacteria and viruses are thereby killed successfully. The germination number of yeasts and fungi is reduced. In a second step, the pH-value is increased and an orally tolerated preservative is added. Yeasts and fungi are thereby killed successfully. The suspension medium used in the second purification step can then be used as a culture medium for additional production (embryonation) and storage.

5 Claims, No Drawings

PRODUCTION OF A VIABLE, STORABLE WORM EGG SUSPENSION

CROSS REFERENCE TO RELATED APPLICATIONS

This application is a national stage application of International Application No. PCT/EP2008/0025412, filed 31 Mar. 2008, which claims the benefit of European Patent Application Serial No. 07006838.2, filed 2 Apr. 2007, from which applications priority is claimed. and which are incorporated herein by reference.

The present invention relates to a purification method for the production of viable suspensions which contain eggs of parasitic helminths, which suspensions are capable of development and are suitable for therapeutic application.

The effect of parasitic infections on the activation of their animal hosts' immune system is known (review, D. M. McKay, Parsitology 2006, 132: 1-12). This activation also influences the appearance and course of diseases of the immune system. Epidemiological studies demonstrate that autoimmune diseases occur more rarely in regions with high worm infection rates than in regions in which these infection rates are lower due to better hygienic circumstances. Cytokin profiles of patients with Crohn's disease, a chronic-inflammatory disease of the intestine, have demonstrated that Th2 immune cells can be stimulated by helminth infections. Crohn's disease, a Th1-dominated autoimmune disease, can be prevented or influenced by an infection with helminths (Summers et al., Am J Gastroenterol 2003, 98: 2034-2041). Other diseases caused by Th1 immune cells, too, are capable of being influenced, as are gastritis caused by *Helicobacter* and autoimmune encephalomyelitis.

Beer (Parasitology 1973, 67: 253-262) has reported as early as in 1973 that *Trichuris suis* may be a suitable nematode for achieving immunization in humans without pathogenic infection with nematodes taking place. *Trichuris suis* is closely related to *Trichuris humanis* and survives in the human gastrointestinal tract, but fails to multiply. Therapeutic measures are not necessary during this self-limiting infection. Infection by *Trichuris suis* can therefore bring about immunization.

R. J. S. Beer (Parasitology 1972, 65: 343-350) describes a method for collecting and purifying worm eggs. Worm eggs in the embryonated state are grown in a 0.2% strength potassium dichromate solution at 32° C. and aerated daily. A similar purification method is described in DE 10 63 115. Worm eggs are freed from any microorganisms and viruses with the aid of hydroxyl-radical- or oxygen-radical-producing chemical reactions. The so-called Fenton reaction is described in particular. In this reaction, $FeCl_2$ is allowed to act on $H_2O_2$ to give nascent oxygen, whose disinfectant activity is exploited.

Boes et al., Veterinary Parasitology (1998), pages 181-190, describe the embryonation and infectivity of eggs of the worm *Ascaris suum* which have been obtained from female worms and which have been embryonated in sulfuric acid.

Summers and coworkers (GUT 2005, 54: 87-90) also purify *T. suis* eggs with a 0.2% strength dichromate solution in phosphate buffer at pH 6-7, after previously having embryonated the eggs for 5-6 weeks in a buffer solution containing antibiotics (pencillin/streptomycin/ampho-tericin B).

The use of such bacteria- and virus-destroying agents has a series of significant disadvantages:
both when using a dichromate solution and when using a Fenton solution, the solution must be removed after a brief period of time so as to avoid damage to the worm eggs. Moreover, experiments have demonstrated that copious multiplication of microorganisms takes place during the embryonation (3 months at 22° C.-25°), which takes place after the purification, despite this preceding purification step, nor can the multiplication of microorganisms be avoided during the subsequent storage of the embyronated eggs at 2-8° C. It is therefore likely that, once such microorganism- and virus-destroying agents have been removed, renewed growth of microorganisms takes place in the *T. suis* egg suspension.

Moreover, the complete removal of dichromate from the solution is absolutely necessary. However, this procedure is very complicated.

While the addition of antibiotics for avoiding copious multiplication of microorganisms during the eggs' embryonation stage, as described by Summers, prevents copious growth of microorganisms in this stage, it is not capable of ensuring the destruction of the microorganisms. After antibiotics have been removed in the subsequent purification and storage steps until use, renewed copious growth of microorganisms is observed.

It is an object of the present invention to prepare an embryonated worm egg suspension which is purified from contaminating viruses and microorganisms, in particular bacteria, and which is capable of being stored without growth of fungal spores and of yeasts taking place. The methods described herein retain the capability of the worm eggs to develop into adult worms. The worm egg suspensions are suitable for therapeutic applications.

Surprisingly, it has been found within the scope of the present invention that a combined purification and preservation method is particularly suitable for solving the above-described problem, since no toxic substances (for example potassium dichromate, $K_2Cr_2O_7$) and no disinfectants are required for this method, in contrast to the previously known methods.

During the purification method, isolated eggs of helminths, preferably of *T. suis*, are incubated in an acid solution, preferably an $H_2SO_4$ solution, at a pH of for a period of 1-72 hours (see example 1). The optimal incubation time is 2 to 8 hours, preferably 3 hours. Incubation is performed at a temperature of from 4° C. to 37° C., preferably from 25° C. to 35° C.

In the process for the preparation of a pharmaceutical preparation capable of being administered orally and comprising a storable suspension of viable eggs of parasitic helminths which are nonpathogenic to humans and where, upon ingestion, a sufficient number of helminths develops to result in the stimulation of regulatory human T-cells, the helminth egg suspension, in a first step, is initially subjected to an acid treatment at a pH of $\leq 2$. In a further step, the pH is raised to $\geq 4$, and a pharmacologically acceptable preservative is added. In principle, it is also possible first to add the preservative and then to carry out the acid treatment. However, it is preferred first to carry out the acid treatment and then to add the preservative.

The acid treatment is preferably brought about by adding sulfuric acid. In the acid treatment, a sufficient amount of acid to lower the pH into a range of between approximately 0.5 and 2 is added. In a further embodiment, the pH is lowered down to approximately 0 to <1. Suitable acids are hydrochloric acid, nitric acid or, preferably, sulfuric acid. The acid treatment may only be carried out over a relatively brief period of time so as to avoid undue damage to the worm eggs. In this context, there is also a relationship between acid concentration and duration of the acid treatment. It is preferred to lower the pH to less than 2, especially preferably even to pH 0.6 to 0.8. The duration of the acid treatment is from several minutes to a few hours, preferably 120 minutes to 360 minutes. The short-term period which is still tolerated includes the embryonation process of the worm eggs (3 months at 22-25° C.).

After the acid treatment, the pH is raised back to a pH of >4 by addition of a suitable base, for example NaOH. Thereafter, one or more preservatives are added, it being possible to employ, in principle, all those substances which are suitable for the preservation of food stuffs or pharmaceuticals. It is preferred to employ those preservatives which are well tolerated precisely by patients with Crohn's disease.

The preservative is preferably selected from the group consisting of sorbic acid, benzoic acid, salts of these acids, parabenzoic acid esters, p-hydroxybenzoic acid esters, propylene glycol, or combinations of these preservatives.

It is especially preferable to employ one or more of the preservatives selected from the group consisting of
  sorbic acid at a concentration of from 0.01 to 0.2%, in particular from 0.1 to 0.2%, benzoic acid at a concentration of from 0.1 to 0.3%,
  p-hydroxy-benzoic acid esters at a concentration of from 0.02 to 0.3% by weight, propylene glycol at a concentration of from 5 to 20% by weight,
  or a combination of the above-mentioned preservatives in the abovementioned concentration ranges.

As an alternative to strong acids, weaker acidic solutions with addition of the above-mentioned preservatives, preferably sorbic acid and its salts, are also suitable for the rapid inactivation of microorganisms and viruses. However, the advantage of using these solutions over using strong acids is that the worm eggs can be purified, embryonated (for 3 months at 22-25° C.), stored and used for patients in a single medium, owing to the less acidic pH. This long-term treatment has no adverse effect on the viability of the worm eggs (see example 5). This mild method uses preservative-containing media with a pH of 1, preferably 2, and results in no limitations with regard to the microbiological purity of the worm egg suspensions.

The resulting preservative-containing suspensions with embryonated worm eggs are suitable for use in patients as a drink. If appropriate, further pharmaceutically acceptable additives such as colorants, flavorings or thickeners may be added to these worm egg suspensions.

The invention therefore relates to pharmaceutical preparations for oral administration, comprising a storable suspension of viable eggs of parasitic helminths which are nonpathogenic to humans, in particular $T.$ $suis$, where, after the ingestion of the suspension, a sufficient number of helminth develops to result in a stimulation of regulatory T-cells, and where the suspension comprises fewer than 1000 colony-forming (cfu=colony-forming unit) microorganisms per ml of suspension. Preferably, the pharmaceutical preparation for oral administration contains fewer than 100 colony-forming units of microorganisms per ml of suspension. Especially preferably, the pharmaceutical preparation for administration contains fewer than 10 colony-forming units of microorganisms per ml of suspension. The number of colony-forming units is determined with the aid of customary microbiological methods.

In the present context, microorganisms are understood as meaning bacteria, viruses, fungi, yeasts and protozoans and no such microorganisms which might have disadvantageous health effects may be present.

The method according to the invention makes it possible to provide the suspension of storable eggs of parasitic helminths which are nonpathogenic to humans in a form in which they are suitable for pharmaceutical administration. The treatment according to the invention firstly destroys contaminating microorganisms, in particular bacteria, but also fungi, viruses and, if appropriate, protozoans, to such an extent that the preparation is suitable for pharmaceutical application. Secondly, however, the treatment is mild enough for the worm eggs to retain their ability of growing, once ingested, in the patient's intestines so as to bring about the desired stimulation of the immune system.

The preparations according to the invention are particularly suitable for the treatment of various inflammatory diseases of the intestine, especially chronic-inflammatory diseases of the intestine. The preparations can be employed in a particularly advantageous manner for the treatment of inflammatory diseases of the intestine referred to as Crohn's disease.

EXAMPLE 1

Depletion of Microorganisms in a Suspension of $T.$ $suis$ Eggs

The microbial count in a $Trichuris$ $suis$ egg suspension (TSO) in phosphate buffer (pH 7) at a concentration of 2400 eggs/ml was determined as specified in the DAB (German Pharmacopoeia, section 2.6.12, last updated with the 24th Supplement in 2006). A microbial count status of 190 000 cfu/ml was found. This suspension was then rebuffered to pH 2 in dilute $H_2SO_4$ solution. After storage for 3 h at 30° C., the microbial count had been reduced to <20 cfu/ml.

The quality of the process presented was then checked. To this end, defined test strains of bacteria, yeast and fungi were used as specified in the German Pharmacopoeia (DAB). Examples 2a, 2b and 2c show the results of this test.

EXAMPLE 2

Determination of the Microbial Count a. A nutrient suspension as specified in DAB 2.6.13 was inoculated with the sporulating and nonsporulating test bacteria detailed in table 1. Then, the mixture was rebuffered to pH 2 using a dilute $H_2SO_4$ solution and stored for 6 h at 30° C. The subsequent determination of the microbial count gave the data shown in table 1.

TABLE 1

| Microorganism | $T_0$ | $H_2SO_4$ pH 2 after 6 h |
|---|---|---|
| Clostridium sporog. | 8 000 000 | <10 |
| Bacillus subtilis | 1 400 000 | 20* |
| Escherichia coli | 130 000 | <10 |
| Staphylococus aureus | 800 000 | <10 |
| Salmonella typhymurium | 250 000 | <10 |

* By extending the acid treatment to approximately 6 to 10 hours, it was possible to reduce the number of colony-forming units to less than 10.

b. A nutrient suspension as specified in DAB 2.6.13 was inoculated with the test yeasts detailed in table 2. Then, the mixture was rebuffered to pH 2 or pH 1 using a dilute $H_2SO_4$ solution and stored for 3 h or 48 h at 25° C. The subsequent determination gave the data shown in table 2.

TABLE 2

| Microorganism | $T_0$ | $T_{3h}$ $H_2SO_4$ pH 2 | $T_{48h}$ | $T_{3h}$ $H_2SO_4$ pH 1 | $T_{48h}$ |
|---|---|---|---|---|---|
| Saccharomyces cer. | 470 000 | 380 000 | 220 000 | 39 000 | 40* |
| Candida albicans | 690 000 | 380 000 | 32 000 | 26 000 | <10 |

*By extending the acid treatment to 72 hours, it was possible to reduce the cfu to 5.

c. A nutrient suspension as specified in DAB 2.6.13 was inoculated with the test molds detailed in table 3. Then, the mixture was rebuffered to pH 2, pH 1 and pH 0 using a dilute $H_2SO_4$ solution and stored for 3 h or 48 h at 25° C. The subsequent determination gave the data shown in table 3.

TABLE 3

| Micro-organism | $T_0$ | $T_{3h}$ $H_2SO_4$ pH 2 | $T_{48h}$ | $T_{3h}$ $H_2SO_4$ pH 1 | $T_{48h}$ | $T_{3h}$ $H_2SO_1$ pH 0 | $T_{48h}$ |
|---|---|---|---|---|---|---|---|
| *Penicillium brevicomp.* | 490 000 | 90 000 | 32 000 | 39 000 | 14 000 | 70 | <10 |
| *Aspergillus niger* | 800 000 | 370 000 | 700 000 | 500 000 | 500 000 | 50 | <10 |

If the cfu of certain microorganisms has not been reduced sufficiently by the acid treatment, the duration of the acid treatment was suitably extended to up to 72 hours.

Examples 1 and 2 a-c demonstrate that, after a brief period of time, bacteria are destroyed efficiently by a dilute $H_2SO_4$ solution of pH 2. Yeasts and fungi require either a longer incubation period or more acidic pH values in order to be destroyed efficiently.

Surprisingly, the above-described purification steps are also suitable for the preparation of a virus-free *T. suis* egg suspension.

EXAMPLE 3

Virus Depletion

Inactivation of murine leukemia virus (MuLV), pseudorabies virus (PRV), porcine parvovirus (PPV) and feline calicivirus (FCV) in the preparation of a *Trichuris suis* egg suspension (TSO). The viruses employed are model viruses.

The virus titers in the inoculated samples were determined by end-point titration. In this method, which is known per se, dilute samples are applied to microtiter plates containing indicator cells which are readily identifiable. After the infection of the indicator cells with the virus-containing samples, the cell morphology changes as the result of cell lysis. This cell lysis can be measured readily under the microscope.

The enveloped and naked test viruses were added in high concentration to an 0.01 $NH_2SO_4$ solution (pH 2, 30° C.) which additionally contains TSO. After 10 min, 3 h and 72 h, the viral activity was determined. After 10 min, the enveloped viruses PRV and MuLV were no longer infectious, and the naked viruses FCV and PPV were no longer infectious after 3 h. The use of a parallel sample neutralized with 1 N NaOH showed that all 4 viruses retained their virulence even after incubation for 3 h. Due to the cytotoxicity of a 0.2% strength potassium dichromate solution in 0.01 N sulfuric acid, it was not possible to test this solution by way of comparison.

A pronounced reduction of fungi and yeasts too was only possible by prolonged incubation and lowering the pH to a value of 0, preferably <1 (see example 2, tables 2 and 3). This purification method in highly acidic medium, which method is novel, has the disadvantage that the viability of a worm egg suspension is adversely affected.

As the second feature of the present invention, it has now been found, surprisingly, that the addition of orally acceptable chemicals used for preservation purposes result in obtaining the embryonation coefficient. The embryonation coefficient is an unambiguous marker for the viability of worm egg suspensions. Moreover, the use of preservatives made it possible to inactivate contaminating microorganisms even at pH 4. Orally acceptable preservatives which have proved to be preferred are benzoic acid, sorbic acid, their salts, and propylene glycol (see example 4a-e).

Only the addition of preservatives makes possible the use of considerably less acidic media, that is media which are better tolerated by the worm eggs. In this manner, the worm eggs can be purified, embryonated, stored and used for the patient in a single medium. A medium for long-term application is therefore available. A possible recontamination of the TSO suspensions with fresh microorganisms can be prevented by using dilute acids and the addition of preservatives. The growth of fresh microorganisms is avoided by the above-described combined method of inactivating and preserving of TSO suspension. Thus, this extremely gentle method has clear advantages over the method based on the use of strong acids.

EXAMPLE 4

Determination of the Colony Number of Various Microorganisms

Raising the pH from pH 2 to pH 4 and addition of preservatives

Experimental conditions for examples 4a to 4e: The test samples contained in each case 10 000 TSO/ml (±10%) in phosphate buffer at pH 4 and either benzoic acid, 0.1% sorbic acid or 15% propylene glycol. The following microorganisms were added to the test samples:

*Aspergillus niger* in the form of an individual microorganism

*Pseudomonas aruginosa, Staphylococcus aureus, Candida albicans* and *Escherichia coli* in combination.

The incubation temperature was 25° C. The test plates were evaluated after 1 to 7 days. The following results were obtained:

| 4 a *Psuedomonas aeruginosa* | | | |
|---|---|---|---|
| Preservative | T 0 (cfu/ml) | T 1d (cfu/ml) | T 7d (cfu/ml) |
| Benzoic acid 0.2% | 180 000 | <10 | <10 |
| Sorbic acid 0.1% | 180 000 | 30 | <10 |
| Propylene glycol 15% | 180 000 | 10 | <10 |
| 4 b *Staphylococcus aureus* | | | |
| Preservative | T 0 (cfu/ml) | T 1d (cfu/ml) | T 7d (cfu/ml) |
| Benzoic acid 0.2% | 130 000 | <10 | <10 |
| Sorbic acid 0.1% | 130 000 | 240 | <10 |
| Propylene glycol 15% | 130 000 | 14 000 | <10 |
| 4 c *Escherichia coli* | | | |
| Preservative | T 0 (cfu/ml) | T 1d (cfu/ml) | T 7d (cfu/ml) |
| Benzoic acid 0.2% | 140 000 | <10 | <10 |
| Sorbic acid 0.1% | 140 000 | 490 | <10 |
| Propylene glycol 15% | 140 000 | 7100 | <10 |
| 4 d *Candida albicans* | | | |
| Preservative | T 0 (cfu/ml) | T 1d (cfu/ml) | T 7d (cfu/ml) |
| Benzoic acid 0.2% | 240 000 | <10 | <10 |
| Sorbic acid 0.1% | 240 000 | 190 | <10 |
| Propylene glycol 15% | 240 000 | 8600 | 30 |
| 4 e *Aspergillus niger* | | | |
| Preservative | T 0 (cEu/ml) | T 1d (cfu/ml) | T 7d (cfu/ml) |
| Benzoic acid 0.2% | 120 000 | 90 | <10 |
| Sorbic acid 0.1% | 120 000 | 20 000 | <10 |
| Propylene glycol 15% | 120 000 | 30 000 | 9000 |

When fungal contamination is severe, it is preferred to employ sorbic acid, benzoic acid and/or p-hydroxybenzoic acid esters, or propylene glycol is employed as a combination with these preservatives.

A further advantage of the combined inactivation of microorganisms by means of dilute acids and the use of preservatives is that recontamination with fresh microorganisms, which is possible, can be prevented during the further use of the TSO suspension. The growth of fresh microorganisms is avoided by the above-described combined method of inactivating and preserving a TSO suspension.

The preparation for the further production and use in patients requires that the pH be raised to a range of pH 2-7, preferably pH 4-6. Again, this third step requires the addition of suitable preservatives.

Preservatives which may be used must be suitable for oral administration. Those which have proved to be suitable for this purpose are sorbic acid at a concentration of 0.1-0.2%, benzoic acid at a concentration of 0.1-0.3%, p-hydroxybenzoic acid ester at concentrations of 0.02-0.3% or propylene glycol as a 5-20% strength aqueous solution. Mixtures of the abovementioned preservatives are also suitable.

Surprisingly, it has been found that the viability of the worm egg suspension is not adversely affected by this purification method.

EXAMPLE 5

Viability of the Worm Eggs

Unembryonated worm eggs at a concentration of 40 000 eggs/ml were suspended in different media and embryonated (22-25° C.). After an incubation time of 60 and 90 days, the individual suspensions were viewed under the microscope, and the embryonation coefficient was calculated based on the total number of worm eggs and the number of morphologically intact and embryonated worm eggs. The embryonation coefficient (EC) is an indicator for the viability of the worm eggs. At the beginning of the embryonation, only unembryonated worm eggs are present, so that the coefficient is zero. It increases during the embryonation period and, at the incubation conditions chosen, reaches its maximum from day 60 onwards. As a rule, values around 90% are obtained.

| Suspension medium | EC Day 0 | EC Day 60 | EC Day 90 |
|---|---|---|---|
| Sulfuric acid pH 1 + 0.01% potassium sorbate | 0 | 0.91 | 0.91 |
| Sulfuric acid pH 1 + 0.07% potassium sorbate | 0 | 0.93 | 0.91 |
| Sulfuric acid pH 0.8 | 0 | 0.94 | 0.90 |
| Sulfuric acid pH 0.5 | 0 | 0.92 | 0.77 |

After an embryonation period of 60 days, a proportion of over 90% embryonated eggs was found for all media. While the preservative-containing media independently of the preservative concentration showed no decrease in the embryonation coefficient after a further 30 days, a drop in the proportion of embryonated worm eggs can already be observed at sulfuric acid pH 0.5. The addition of orally tolerated preservatives, preferably sorbic acid and its salts, therefore permits the use of pH values which are harmless to the worm eggs. This method can therefore be employed for producing a preparation which is suitable for stable storage (gentle method).

The preparation for the further production requires that the pH be raised to a range of pH 2-7, preferably pH 4-6, and that suitable preservatives be added. The preservatives to be used must be suitable for oral administration. Those which have proved to be suitable for this purpose are sorbic acid at a concentration of 0.1-0.2%, benzoic acid at a concentration of 0.1-0.30, or propylene glycol as a 5-20% strength aqueous solution. Mixtures of the abovementioned preservatives are also suitable.

The invention claimed is:

1. A process for the preparation of a non-pathogenic pharmaceutical preparation of a storable suspension of viable parasitic *Trichuris suis* eggs for oral administration comprising:
    obtaining viable eggs from *Trichuris suis*;
    subjecting said eggs to sulphuric acid treatment at a pH of ≤2 for a period of 2 to 8 hours;
    adjusting the pH to ≥4 by adding a suitable base; and
    adding a pharmacologically acceptable preservative,
    wherein after the ingestion of the suspension of eggs by a human, a sufficient number of helminths develop which result in a stimulation of regulatory human T-cells.

2. The process as claimed in claim 1, characterized in that the preservative is selected from the group consisting of sorbic acid, benzoic acid, salts of these acids, p-benzoic acid esters, propylene glycol, and a combination of these preservatives.

3. The process as claimed in claim 2, characterized in that one or more preservatives selected from the group consisting of sorbic acid at a concentration of from 0.01 to 0.2%, benzoic acid at a concentration of from 0.1 to 0.3%, p-hydroxy-benzoic acid esters at a concentration of from 0.02 to 0.3% by weight, propylene glycol at a concentration of from 5 to 20% by weight and a combination of the abovementioned preservatives in the abovementioned concentration ranges is added.

4. The process as claimed in claim 1, characterized in that further pharmaceutically acceptable additives are added to the suspension.

5. The process as claimed in claim 1, characterized in that the acid treatment is brought about by addition of sulfuric acid.

* * * * *